United States Patent [19]

Majeed et al.

[11] Patent Number: 5,783,603
[45] Date of Patent: Jul. 21, 1998

[54] POTASSIUM HYDROXYCITRATE FOR THE SUPPRESSION OF APPETITE AND INDUCTION OF WEIGHT LOSS

[75] Inventors: Muhammed Majeed; Vladimir Badmaev, both of Piscataway, N.J.; R. Rajendran, Bangalore, India

[73] Assignee: Sabinsa Corporation, Piscataway, N.J.

[21] Appl. No.: 829,143

[22] Filed: Mar. 31, 1997

Related U.S. Application Data

[63] Continuation of Ser. No. 440,968, May 15, 1995, abandoned.

[51] Int. Cl.⁶ .................................................. A61K 31/19
[52] U.S. Cl. ............................................ 514/574; 514/909
[58] Field of Search ................................................. 514/574

[56] References Cited

U.S. PATENT DOCUMENTS 3,764,692  10/1973  Lowenstein .......................... 424/279
5,536,516   7/1996  Moffett et al. ....................... 426/271

OTHER PUBLICATIONS

Sullivan et al, *Chemical Abstracts,* vol. 81, No. 4, Abstract #21740d, 1974, p. 110.

Sullivan et al, *Chemical Abstracts,* vol. 87, No. 3, Abstract #20073a, 1977, p. 399.

McCarty, *Chemical Abstracts,* vol. 121, No. 9, Abstract #104969f, 1994, p. 670.

*Primary Examiner*—William R. A. Jarvis
*Attorney, Agent, or Firm*—Nikaido Marmelstein Murray Oram, LLP

[57] ABSTRACT

The present invention provides methods of suppressing appetite and causing weight loss by administering to a patient hydroxy citric acid in the form of a potassium salt extracted from Garcinia fruit. Methods of inhibiting cytoplasmic citric lyase and increasing fat metabolism in a patient are also described.

9 Claims, 4 Drawing Sheets

POTASSIUM HYDROXYCITRATE FOR THE SUPPRESSION OF APPETITE AND INDUCTION OF WEIGHT LOSS

This application is a continuation of application Ser. No. 08/440,968, filed May 15, 1995, now abandoned.

BACKGROUND OF THE INVENTION

1. Field of the Invention

The invention is directed to a new process for making hydroxy citric acid in a form that is stable and biologically active. Compositions containing the potassium hydroxy citric acid are useful as natural appetite suppressants.

2. Description of Related Art

During the 1970s, scientists at Brandeis University and at Hoffman LaRoche demonstrated that synthetic hydroxycitric acid, when blended with the diet, had a marked suppressive effect on weight gain in rats. The researchers noted that the HCA-treated rats tended to eat less; food consumption was suppressed by 10% or is more on optimal HCA intakes, that is, when HCA constituted 1% or more of the diet.

The mechanism by which the HCA affected weight gain was not known. Since the brain uptake of HCA appeared to be negligible, scientists speculated that the appetite-suppressive effect of HCA was exerted not through central nervous system (CNS) action, but rather by directly affecting the metabolic processes of the organism.

One of the most metabolically active organs in the body is the liver. One important function of the liver is to insure that the blood maintains adequate concentrations of glucose to fuel the body's energy requirements. The liver can store dietary glucose in the form of the polysaccharide glycogen, and release glucose when blood glucose levels are low. The liver can also synthesize glucose in a complex process known as gluconeogenesis, from either amino acids or lactic acid as starting material. This newly synthesized glucose can either be released into the blood stream to supply energy requirements of body tissues, or can be stored as glycogen for future use.

The direct parasympathetic connection between the liver and the CNS monitors the level of glucose and glycogen in the liver. A high level of glycogen, as a result of high glucose supply, is translated by the CNS as the state of satiety, which results in decreased craving for food.

Since increased glycogen in the liver aids satiety, the effect of HCA on gluconeogenesis in rat liver has been studied. It has been found that the rate of gluconeogenesis, from lactate or the amino acid alanine, was approximately doubled in HCA-treated rats. This result provides support for the idea that HCA causes the observed appetite suppression via altering the rate of gluconeogenesis.

However, it appears unlikely that reduction of food intake can entirely account for the substantial reductions in weight gain seen in HCA-treated rats. For example, in one study, the net reduction in food consumption during the 80 day study period amounted to only 4%—and yet the rats had gained 78% less weight than the controls over this period. Other studies, providing less dramatic results, suggested that the reduction of weight gain was disproportionately large compared to the reduction in food consumption.

Because of this discrepancy between considerable weight loss versus a meager appetite suppression, it has been postulated that HCA exerts a mechanism which increases fat burning, which in turn could decrease body weight, in addition to affecting gluconeogenesis.

Fat burning, or oxidation, plays a prominent role in liver metabolism. Liver metabolic activity accounts for over a quarter of the total body oxygen consumption in a subject at rest. The substantial energy needs of the liver are met largely by oxidation of fat. The dietary fat is absorbed by liver cells, which oxidize or burn it for energy in the mitochondria. The fats are transported from the cell cytoplasm into the liver mitochondria, by linking them to the special transporting molecule L-carnitine. This reaction is facilitated by the enzyme carnitine acyltransferase.

Carnitine acyltransferase is inhibited by malonyl CoA, which can be obtained from conversion of acetyl CoA. Malonyl CoA, can not only inhibit the fat burning process, but also increase the body fat synthesis, since it is the direct precursor for the synthesis of fat and cholesterol. The acetyl CoA is synthesized in mitochondria, but it has to be transported to the cell cytoplasm to exert its biochemical action. However, it cannot be transported to the cytoplasm from mitochondria before it is converted to citric acid. Thus, citric acid is a transportable form of acetyl CoA. Citric acid, once in the cytoplasm, is converted to acetyl CoA with the help of the enzyme—citrate lyase. HCA was found to be an extremely potent competitive inhibitor of citrate lyase ($K_i$ = 0.15 µM). The affinity of the enzyme for HCA was over a hundred times greater than the affinity of the enzyme for citric acid. This action was afforded only by a HCA in a pure acid form, but not in the lactone form.

The significance of citrate lyase inhibition by HCA is that without active citrate lyase, little acetyl CoA could reach the cytoplasm. This in turn would limit the availability of malonyl CoA and slow the synthesis of fats and cholesterol, while disinhibiting the metabolic breakdown of fat, or oxidation of fat.

In light of the considerations noted above, it is likely that the ability of HCA to promote fat loss in humans results primarily from the stimulation of fat oxidation.

Activation of fat oxidation in the liver also tends to stimulate gluconeogenesis, primarily due to increased activity of the key enzyme pyruvate carboxylase. This in turn may replenish the stores of liver glycogen, and send a message of satiety to the brain center.

The drawbacks of HCA use as a weight loss compound stem from the following problems:

1. The poor technology of HA extraction from the fruit of Garcinia cambogia often provides HCA in lactone form, which is inactive, or less active, in inhibiting the citrate lyase;
2. The HCA, if not stabilized chemically, has natural propensity to be converted to the lactone form in aqueous solutions and in the gastrointestinal tract, i.e., without absorption of HCA in pure acid form, the HCA can not inhibit the citrate lyase; and
3. High concentrations of HCA, that is, 1% or more (by weight) of the daily dietary intake, are required to exert the metabolic activity, because of poor cellular uptake. Without absorption of HCA, and the presence of HCA in the cytoplasm in pure acid form, HCA can not inhibit citrate lyase and exert its inhibitory activity on acetyl CoA formation.

In the past, it has been difficult to isolate hydroxy citrate in a form which is both stable and biologically active. Hydroxy citric acid exists in two forms, the free acid form and the lactone form. The free acid form is biologically active and the lactone form is inactive. However, the free acid form is not stable and gets converted to its lactone form, which is stable but inactive.

One prior art isolation procedure, that of Y. S. Lewis et al., in Phytochem 1965, Vol. 4, pp. 610–625, results in the isolation of hydroxy citric acid lactone.

I. WATER EXTRACT OF (−) HYDROXYCITRIC ACID FROM FRUIT OF GARCINIA CAMBOGIA (Lewis, Y. S. and Neelakantan, S., phytochemistry (1965) Vol. 4; pp. 619–625)

The prior art procedure to obtain (−)HCA from Garcinia cambogia on a large scale included the following procedure:

1. The dried rind was cooked with about three volumes of water in an autoclave (10 lb/in$^2$) for 15 minutes;
2. The resulting extract was filtered through a cloth and then through a paper filter;
3. The obtained filtrate was concentrated to a small volume, and the alcohol precipitation method removed pectin contamination;
4. The clear filtrate was then treated with potassium hydroxide (alkali) to form viscous, dark, heavy liquid; this treatment resulted in formation of a hygroscopic material consisting of potassium salt of hydroxycitric acid;
5. The clear supernatant was decanted off and the oily liquid washed with 60% alcohol several times;
6. By repeated treatment with absolute alcohol, the material could be dried to a pale yellow hygroscopic powder, which formed pure alkali salt;
7. Aqueous solutions of the alkali salt were passed through a cation-exchange resin (Zeocarb 215) for recovery of the acid;
8. The obtained (−)HCA was chemically unstable, and upon evaporation formed lactone.

Another process for isolation of lactone was reported by Y. S. Lewis.

II. ACETONE EXTRACT OF (−) HYDROXYCITRIC ACID FROM THE FRUIT OF GARCINIA CAMBOGIA (Lewis, Y. S. (1981) Methods in Enzymology, Vol. 77; Published by Academic Press; pp. 613–619).

1. One kg of fruit of *Garcinia cambogia* is kept in 1500 ml of acetone in an overnight;
2. The fruit is re-extracted in a similar manner;
3. Acetone is removed from the combined extracts by distillation;
4. The viscous residue is stirred with 1 liter of water at 45°–50° C.;
5. The mixture is filtered through cheesecloth;
6. The precipitated insoluble material is removed by filtration;
7. The reddish brown filtrate is treated with activated charcoal at 80°–90° C. and concentrated to a thick syrup;
8. The syrup is "seeded" with a few crystals of the lactone and left overnight;
9. The yield is vigorously extracted with 3 liters of ether;
10. The combined extracts are dried over anhydrous sodium sulfate;
11. Ether is then removed, and the remaining material is white solid, consisting mainly of lactone. The yield is approximately 150 gm.

SUMMARY OF THE INVENTION

The principle of the present invention is to provide technology for extraction of HCA in pure acid form, and technology for chemical modification of HCA to afford chemically stable product, which will not convert into lactone form, which will not be hygroscopic, and which is soluble in aqueous solutions and easily absorbable by the gastrointestinal tract.

The invention provides HCA by combining it with potassium into potassium hydroxycitrate—a water soluble salt. Potassium is an ion primarily found in the cell cytoplasm, and it can easily cross from outside the cell to inside the cell. The cell membrane permeability for potassium is 100 times higher than for sodium and 25 times higher than for chloride. Potassium salt of HCA acts as a transporter of HCA inside the cell, where the biochemical action of HCA is exerted.

DESCRIPTION OF THE PREFERRED EMBODIMENTS

Process Outline

Figure 1:
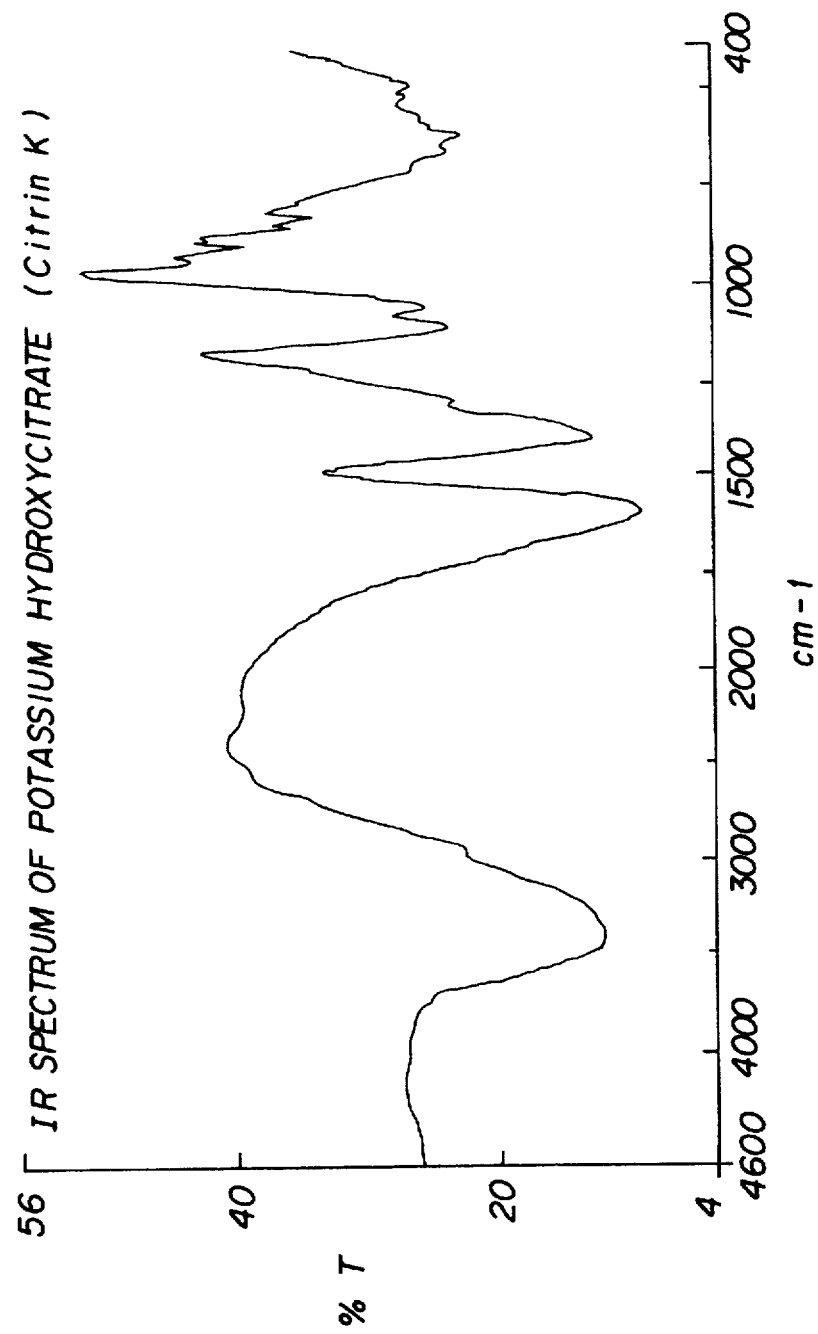
FIG. 1 is an infrared spectrum of potassium hydroxy citrate.

The process of the present invention is used to isolate hydroxy citric acid as potassium hydroxy citrate from a natural source of Garcinia species. Preferred sources include Garcinia cambogia and Garcinia indica.

Briefly, fruit of the Garcinia species is extracted with an alkyl alcohol. Preferred alcohols include methyl alcohol, ethyl alcohol, propyl alcohol, and isopropyl alcohol. Especially preferred is methanol. The extract is treated with a suitable alkali to precipitate the potassium hydroxy citrate. Preferred alkalis include potassium hydroxide, potassium carbonate, etc. Most preferred alkali is potassium hydroxide.

The general process includes the following steps. Garcinia fruit is extracted with an alkyl alcohol at above ambient temperature. This is done at or above atmospheric pressure. The extract is collected. The extraction step is repeated at least three times. The extracts are combined and treated with an alcoholic solution containing alkali. The resultant mass is heated to above ambient temperature and pH is adjusted to make the solution alkaline. The pH of the solution is normally between 8 to 11.5. The product is filtered and washed with alcohol. The product is dried at or above 25° C. under vacuum or at atmospheric pressure or under inert atmosphere, like nitrogen. The dried product is milled, sifted, blended and packed under nitrogen blanket to obtain product. The yield from 500 kgs of garcinia fruit ranges from 60 to 150 kgs of potassium hydroxy citrate based on the hydroxy citric acid content present in the fruit.

Unique Aspects of our Process

Hydroxy citric acid exists in two forms, i.e., free acid form and lactone form. The free acid form is biologically active and the lactone form is inactive. However, the free acid form is not stable and this gets converted to its lactone form, which is stable but inactive. In our process, the free acid form is isolated and stabilized as potassium salt to retain the activity. This is one of the unique aspects of our process.

Another unique aspect of our process is that our potassium hydroxy citrate is water soluble and therefore, it is readily available in the biological system for its bioefficacy.

EXAMPLE

The detailed procedure used to obtain the product trademarked at CITRIN®-K is as follows:

1. The 500 kg of Garcinia fruit is extracted with 1500 l of methanol at about reflux temperature for 3 hours;
2. This is filtered through the cloth filter to collect the first extract;
3. Additional 1500 l of methanol is added to the Garcinia fruit and refluxed for about 3 hours;
4. This is filtered to collect the second extract;
5. The 1500 l of methanol is added again to the Garcinia fruit and refluxed for 3 hours;
6. This is filtered, and the third extract is collected;
7. All the three extracts are combined;
8. The combined extracts are treated with methanolic potassium hydroxide at pH 10;
9. This is again refluxed for about 3 hours to attain constant pH 10 to precipitate potassium hydroxycitrate;
10. The precipitate is filtered and washed with 500 l of methanol;
11. The precipitate is dried under vacuum at about 70° C.;
12. The dried product is milled, sifted, blended and packed under nitrogen blanket to obtain product trademarked at CITRIN®-K;
13. The methanolic mother solution is distilled to recover methanol;
14. The yield from 500 kg of Garcinia fruit is about 150 kg of potassium hydroxycitrate.

The specifications of the product CITRIN®-K is given below:

Specifications

Molecular Structure
Molecular Formula $C_6H_5K_3O_8 \cdot H_2O$
Molecular weight 340.41
Description Beige to pale brown colored powder
Solubility Soluble in water, acids and aqueous alcohols.
 Insoluble in solvents like methanol, alcohol, chloroform, benzene, etc.
Loss on Drying Not less than 3% and not more than 6.0%
pH of 5% solution 7.0 to 9.0 in water
Specific Rotation $-18°$ to $-25°$ on anhydrous basis
Potassium content not less than 30% by weight on anhydrous basis
Hydroxy citric Not less than 50% on anhydrous basis acid content
Lactone content (HPLC) less than 2% by weight

Identification a) By IR Spectrum

The infrared absorption spectrum of a potassium bromide dispersion of potassium hydroxy citrate, previously dried, exhibits maxima only at the same wavelength as that of similar preparation of Working Standard. IR Spectrum of Potassium Hydroxy Citrate Working Standard is shown in FIG. 1.

b) For Potassium

Produces yellow or orange-yellow precipitate with sodium cobaltinitrite solution.

Dissolve 50 mg of 1 ml of water, add 1 ml of dilute acetic acid and 1 ml of freshly prepared 10% w/v solution of sodium cobaltinitrite. A yellow or orange-yellow precipitate forms immediately.

c) For Citrate

Dissolve 0.5 g in a mixture of 10 mL of water and 2.5 mL of 2N nitric acid. Add 1 mL of mercuric sulphate solution heat to boiling, and add 1 mL of potassium permanganate solution: a white precipitate is formed.

d) By Paper Chromatography
 Mobile Phase
 Butanol (4): Acetic Acid (1): Water (5)

Prepare 100 mL of mobile phase in separator and mix well. Allow it to separate and use the upper layer as mobile phase.

Stationary Phase:
 Whatman filter Paper No. 1
 Sample Preparation

Dissolve 100 mg of the sample in 1 mL of water and dilute to 10 mL with methanol in a volumetric flask.

Standard Preparation

Dissolve 100 mg of the Working Standard in 1 mL of water and dilute to 10 mL with methanol in a volumetric flask.

Procedure

Apply separately equal volume (10 μl) of sample and standard preparation and develop the chromatogram in the chamber previously saturated with mobile phase. After developing the chromatogram to ¾, the paper is removed and dried in a current of air.

Detection

The paper is sprayed with sodium metavanadate solution (5% w/v) and observed for the orange spot. The Rf value of the spot obtained from the sample solution is same as that of the Standard solution.

LOSS ON DRYING

Limit: Not less than 3.0% and not more than 6.0%

The material shows weight loss of about 5% when dried at 150° C. under vacuum for four hours. This weight loss is due to the release of water of hydration from the molecule.

THERMAL ANALYSIS

Potassium hydroxy citrate is analyzed by Thermogravimetry. This technique is used to estimate the presence of water of hydration in the product. The details of the methods are given below:

In this method, the sample is heated under nitrogen/argon atmosphere and the weight loss is recorded continuously.

Limit: The weight loss is not more than 6.0%

Analysis is carried out using about 3 mg of the sample accurately weighed. The temperature setting is from 30° C. to 400° C. with the rate of heating as 10° C. per minute. The heating of the sample is done under nitrogen/argon atmosphere flowing at a flow rate of 40 mL/min.

From the TGA thermogram, it is observed that there is weight loss between 180° C. and 250° C. to a level of about 5% which indicates the presence of water of hydration.

The percentage loss corresponds to one molecule of water.

Figure 2:
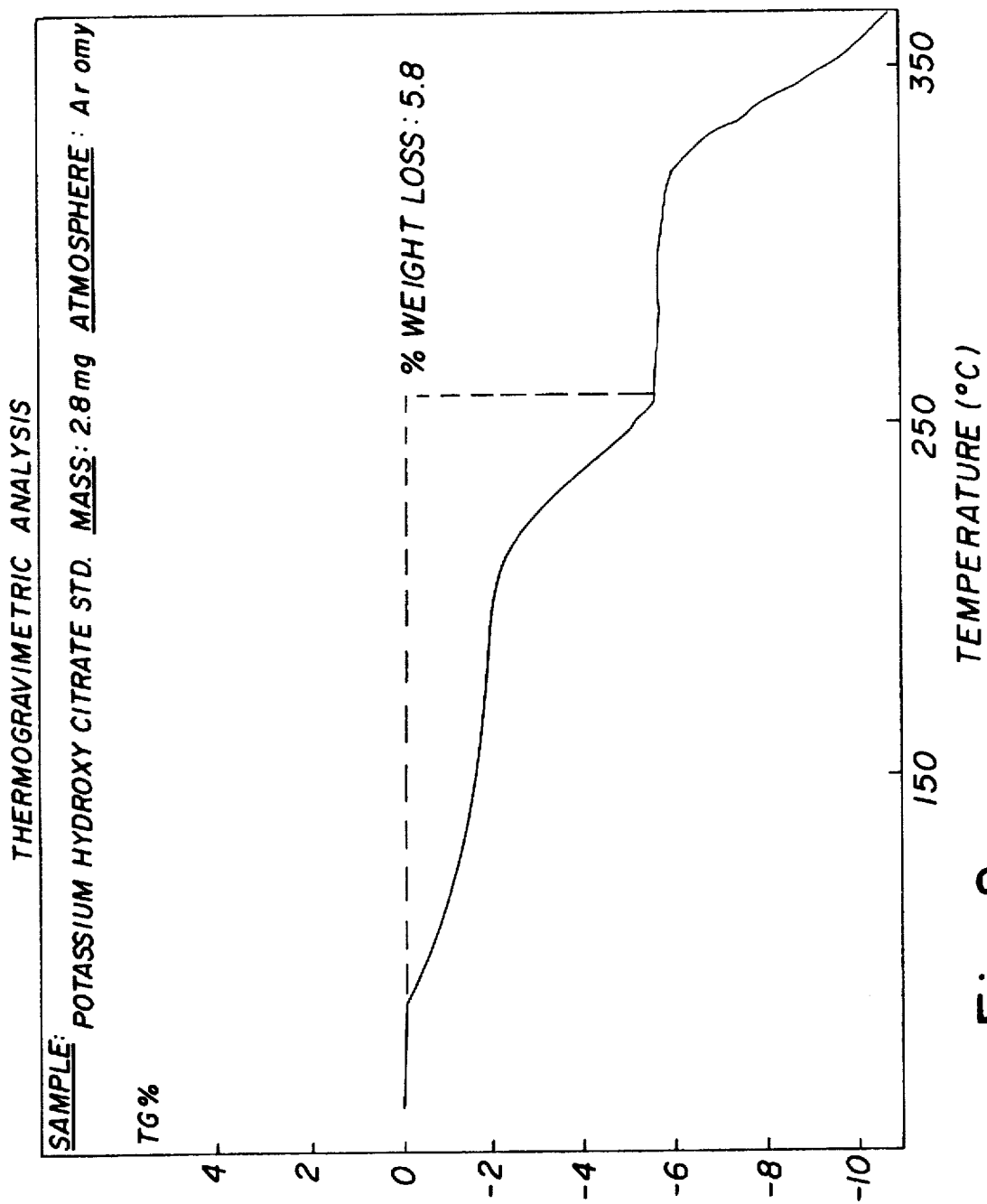
FIG. 2 is a thermogram of potassium hydroxy citrate.

A typical thermogram is given in FIG. 2.

pH OF SOLUTION pH of 5.0% w/v solution is between 7.0 and 9.0.

Dissolve 2.5 g in 50 ml of water and determine the pH using suitable calibrated pH meter.

SPECIFIC ROTATION

Between $-18.0°$ and $-25.0°$ calculated on anhydrous basis.

Weigh accurately about 1 g of the sample and transfer into a 100 ml volumetric flask, dissolve in water, dilute to volume and mix.

Measure the rotation using suitable polarimeter at about 25° C.

ASSAY

Assay of the product is estimated by estimating the content of HYDROXY CITRIC ACID and POTASSIUM.

For determination of HYDROXY CITRIC ACID, the following methods are employed:
 i) TITRATION METHOD
 ii) HPLC METHOD The details of the methods are given below: Limit: Content of HCA is not less than 50.0% calculated on anhydrous basis

TITRATION METHOD

Weigh accurately about 200 mg of the sample and transfer into a beaker. Add 100 ml of water and dissolve. Pass the solution through cation ion exchange resin column and collect the affluent into a 1 L flask. Rinse the beaker with water and pass the washings through the column. Wash the column with distilled water until the elute shows a pH of 4.0 to 4.5. Adjust the volume to about 500 ml and titrate with 0.1N sodium hydroxide solution using phenolphthalein solution as indicator.

Perform a blank titration after eluting 500 ml of water through the column.

Calculation:

(Titre value–blank value)×0.1N of NaOH×0.006933×100×100 0.1
×Weight of the sample×(100–LOD)

Note 1 Column Preparation and Regeneration:
 About 75 g of cation exchange is packed in a column of 2 cm diameter. Soak the column for 30 minutes in 2N Hcl. Wash thoroughly with distilled water to get a pH of 4.0 to 4.5
 After the analysis, the cation exchange resin is soaked with 2N Hcl for 3 hours. It is then washed well with distilled water until the pH of the washings shows 4.0 to 4.5

Note 2 The above method is based on the published research paper titled "Chemical Constituents of Kokum Fruit Rind" by CFTRI, Mysore.

Figure 3:
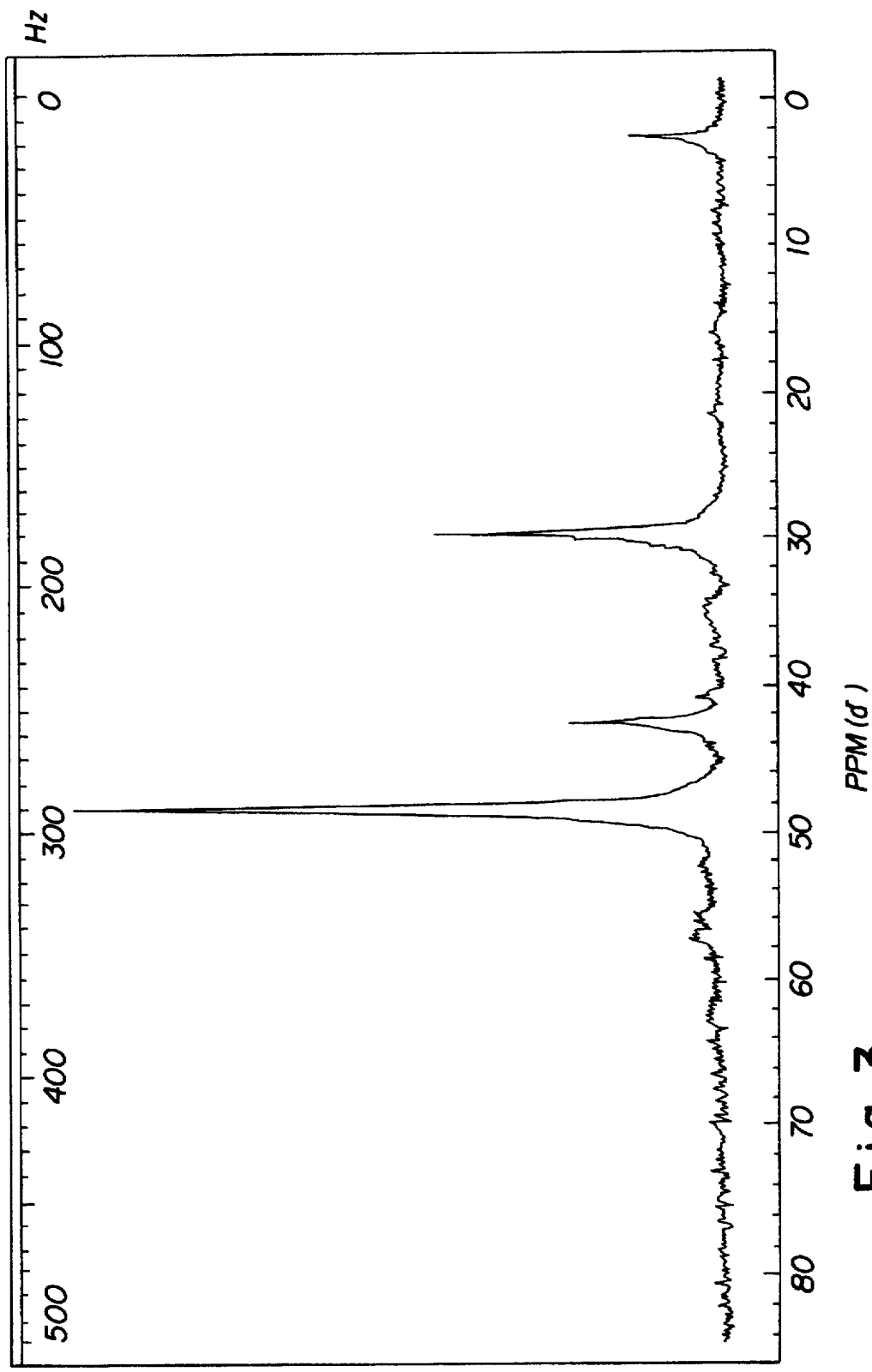
FIG. 3 is a NMR spectrum of potassium hydroxy citrate.

Note 3 Specification of the cation exchange resin is given in FIG. 3

Note 4 The factor of 0.006933 is arrived at by the following calculation $(C_6H_8O_8) + 6\ NaOH \rightarrow \rightarrow Na_6(C_6H_5O_8) + 6H_2O$

[2 moles of HCA].
416 g of HCA ≡ 6000 ml of 1N NaOH or
6000 ml of 1N NaOH ≡ 416 g of HCA $1\ ml\ of\ 1\ N\ NaOH \equiv \frac{416}{6000} = 0.06933\ g$ $1\ ml\ of\ 0.1\ N\ NaOH = \frac{0.06933}{10} = 0.006933\ g$

HPLC METHOD

Figure 4:
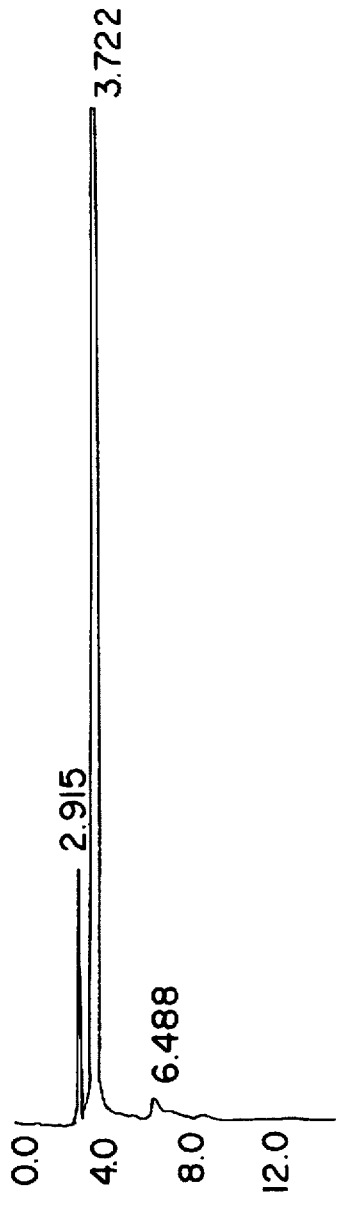
FIG. 4 is an HPLC chromatogram of Potassium Hydroxy Citrate

In this method, normally, (−) Threo Hydroxy Citric Acid Ethylene Diamine Salt (Fluka Standard) is used as a Standard to estimate Hydroxy Citric Acid content in Potassium Hydroxy Citrate. This Standard is not readily available, and therefore an alternate standard, Potassium Hydroxy Citrate is preferred. A pure sample of Potassium Hydroxy Citrate has been synthesized and validated against the Fluka Standard (FIG. 4). In the method given below, Potassium Hydroxy Citrate is used as a Working Standard (WS).

Mobile Phase
 Prepare 0.01N sulfuric acid, filter and degas.
Sample Preparation
 50 mg of the sample is accurately weighed, dissolved in water and diluted to 25 ml with water.
Standard Preparation
 50 mg of Potassium Salt of Hydroxy Citric Acid (WS) is dissolved in 10 ml of water, and diluted to 25 ml with water.
Chromatographic system
 The liquid chromatograph is equipped with 210 nm detector and a 4.6×250 mm organic acid column (Vydac make). The flow rate is about 1 ml per minute. Chromatograph the standard preparation and calculate the Relative Standard Deviation (RSD) for replicate injections. The RSD is not more than 2.0%.
Procedure
 Separately inject equal volume (20 μl) of sample and standard preparation and record the responses obtained for the major peaks.
Calculation:

$$\frac{\text{Area of the sample} \times \text{standard weight} \times (100 - \text{water content of } STD \times HCA \text{ content of standard})}{\text{Area of the standard} \times \text{sample weight} (100 - LOD \text{ of Sample})} =$$

Hydroxy Citric Acid content in the sample

ESTIMATION OF POTASSIUM

This estimation is done by two methods:
 i) FLAME PHOTOMETRY
 ii) ATOMIC ABSORPTION The details of the methods are given below:
Limit of Potassium: Not less than 30.0% calculated on anhydrous basis

FLAME PHOTOMETRY

Standard Stock Solution
 Weigh accurately about 1.84 g of Potassium Chloride, previously dried at 105° C. for 2 hours and transfer into a 250 ml volumetric flask, add water to volume and mix.
Lithium Diluent Solution
 Transfer 1.04 g of Lithium Nitrate to a 1000 ml volumetric flask, add a suitable nonionic surfactant, add water to volume and mix
Standard Preparation
 Pipette 5 ml of stock solution into a 50 ml of volumetric flask, dilute to volume with water and mix. Transfer 5 ml of this solution to a 100 ml volumetric flask and dilute with lithium diluent solution to volume and mix.
Assay Preparation
 Weigh accurately about 3 g of the sample and transfer into a 250 ml volumetric flask, add water to dissolve and dilute to volume and mix. Pipette 5 ml of this solution into a 50 ml volumetric flask, add water to volume and mix. Transfer 5 ml of this to a 100 ml volumetric flask, dilute with lithium diluent solution to volume and mix.
Procedure
 Using a suitable flame photometer adjust to read zero with lithium diluent solution concomitantly determine the emission readings for Standard and Sample preparations at about 766 nm Calculate the content of Potassium as follows:

$$\frac{\text{Emission reading of Standard} \times \text{Weight of Standard} \times 39.1}{\text{Emission reading of Sample} \times \text{Weight of Sample} \times 74.55}$$

ATOMIC ABSORPTION

Potassium Stock Solution
 Dissolve 190.7 mg of potassium chloride, previously dried at 105° C. for 2 hours, in water. Transfer to a 500 ml volumetric flask, dilute with water to volume and mix. transfer 5 ml of this solution to a 100 ml volumetric flask. dilute to volume with water and mix.

Standard Preparation

To separate 100 ml volumetric flask, transfer 10, 15 and 20 ml respectively of Potassium stock solution. To each flask, add 2 ml of sodium chloride solution (1 in 5) and 1 ml of hydrochloric acid, dilute with water to volume and mix.

Assay Preparation

Weigh accurately about 1 g of the sample and transfer into a 500 ml volumetric flask dissolve in water, dilute to volume and mix. Transfer 5 ml of this to a 100 ml volumetric flask, dilute to volume with water and mix. Transfer again 5 ml of this solution to a 100 ml volumetric flask, add 2 ml of sodium chloride solution (1 in 4) and 1 ml of hydrochloric acid. Dilute with water to volume and mix.

Procedure

Concomitantly determine the absorbencies of the Standard preparations and assay preparation at the potassium emission line of 766.5 nm, with a suitable atomic absorption spectrophotometer equipped with a potassium hollow cathode lamp and an air acetylene flame, using water as the blank. Plot the absorbance of standard preparation versus concentration in µg per ml of potassium and draw the straight line best fitting the three plotted points. From the graph so obtained, determine the concentration, in µg per ml of potassium in the assay preparation.

Calculate the content of potassium in mg as follows: 200×C where 'C' is concentration in µg per ml Calculate the percentage of potassium as follows:

$$\frac{200 \times 'C' \times 100}{\text{Wt. taken in mg}}$$

MICROBIAL ASSAY

Total Plate Count, *E. coli*, Salmonella, yeasts and molds are estimated as per procedures described in "OFFICIAL METHODS OF ANALYSIS—ASSOCIATION OF OFFICIAL ANALYTICAL CHEMISTS" (14th Edition, 1990)

The limits are given below:

| Total Plate Count | 10000 cfu/g |
| E. coli | Absent |
| Salmonella | Absent |
| Yeasts/Molds | 1000 cfu/g |

Aflatoxins are estimated by the following procedure, which is based on the methods described in "OFFICIAL METHODS OF ANALYSIS—ASSOCIATION OF OFFICIAL ANALYTICAL CHEMISTS" (15th Edition 1990)

Limit: Aflatoxins—Not more than 20 parts per billion

Procedure for estimated Aflatoxins

Apparatus

High speed stirrer (1400–1600 rpm with stainless steel shaft and propeller blade)

Ultra Violet Light

Long wave UV with intensity of 430 µ watt/cm$^2$ at 15 cm at 365 nm

Minicolumn

Borosilicate std wall tubing, Ca 6(id)×200 nm tapered at one end to ca 2 mm

Densitometer

With fluorometry attachment

Reagents

Distilled water or deionized water may be used.

a) Solvents $CHCl_3$ and acetone AR grade must be used b) Potassium hydroxide wash solution 0.02N KOH with 1% Kcl. Dissolve 1.12 g KOH pellets and 10 g Kcl in 1 L $H_2O$ c) Sodium hydroxide solution 0.02N 8.00 g of $NaOH/LH_2O$ d) Sulphuric acid solution—0.03%

Dilute 0.3 ml $H_2SO_4$ to 1 L e) Precipitating reagents i) Copper carbonate, basic ii) Ferric chloride slurry: Mix 20 g anhydrous $FeCl_3$ with 300 ml $H_2SO_4$ f) Diatomaceous earth Hyflo Super-Cel or equivalent g) Column Packing Silica Gel G 60–100 mesh; Florisil 100–200 mesh; Alumina neutral 80–200 mesh; $CaSO_4$ anhydrous 20–40 mesh h) Aflatoxin Standard solutions Standards from Sigma Chemicals, USA, are used.

Preparation of Mini Column

Tamp small plug of glass wool into tapered end of column. To column, add to height indicated in following order: 30 mm silica gel; 10 mm neutral alumina and 10 mm $CaSO_4$. Tamp small plug of glass wool on top of column. Tamp column after each addition to settles packing and maintain interfaces as level as possible. After packing, apply pressure to top glass wool plug with 5 mm diam. rod. Activate packed columns at 110° C. for 1–2 hours and store in vapor tight container.

Extraction of Aflatoxins

Weigh 50 g sample into stirrer, add 250 ml $CHCl_3$—$H_2O$ (85+15) and stir it for 30 minutes. Filter through Whatman No. 4 filter paper. Collect 150 ml filtrate and transfer to 500 ml beaker.

Purification

To 50 ml beaker, add 170 ml 0.2 N NaOH and 30 ml $FeCl_3$ slurry and mix well. Add 3 g basic $CuCO_3$ to sample extract in 500 ml beaker and mix well, add both 1 and 2 mixtures and mix well. Filter the mixture through Whatman No. 4 filter paper in a Buchner funnel using Hyflo supercel bed.

Transfer 150 ml filtrate to 500 ml separator, add 150 ml 0.03% $H_2SO_4$ and 10 ml $CHCl_3$. Shake vigorously for 5 minutes and allow to stand for 30 minutes. Transfer lower $CHCl_3$ layer (13–14 ml) to 125 ml separator. Add 100 ml KOH wash solution, swirl gently for 30 seconds and allow to stand. (If emulsion occurs, drain emulsion into 10 ml test tube add 1 g anhydrous $Na_2SO_4$, stopper, shake 30 seconds and allow to stand ($CHCl_3$ phase need not be completely clear). If emulsion is not broken, transfer emulsion to 125 separator and wash with 50 ml 0.03% $H_2SO_4$. Collect 3 ml $CHCl_3$ layer in 10 ml test tube.

Column Chromatography

Transfer 2 ml $ChCl_3$ solution (extract) to minicolumn, using 5 ml syringe. Hold the column vertically and apply slight air pressure (with the help of a rubber bulb) to force solvent through column at rate ≤10 cm/min until solvent appears at tip. Remove rubber bulb and add about 5 ml of elution solvent containing $CHCl_3$—acetone (9:1). Collect the fractions.

Examine column under UV lamp for blue fluorescent band at top of Florisil layer (Ca 2.5 cm from bottom of column) indicative of aflatoxin. Collect the fractions corresponding the blue band separately and concentrate to a residue.

TLC

Dissolve the residue in minimum quantity of $CHCl_3$ and carry out the TLC testing along with authentic sample of Aflatoxins. Solvent system—Benzene: Methanol: Acetic Acid (95:5:5). Quantify the aflatoxin by using TLC densitometer.

STABILITY

The stability of the product was evaluated in solid state and in aqueous solution in temperature and humidity conditions as specified below. The following parameters of the product were considered: physical appearance, specific rotation, HCA content by HPLC, lactone content by HPLC.

1. In solid state:
   a) Room temperature,
   b) 37° ±2° C. and 75%±2 relative humidity
   c) 45° ±20° C. and 75%±2 relative humidity
2. In solution form (5% in water)
   a) Room temperature
   b) 37° ±20° C.
   c) 45° ±2° C.

Conclusion

The product is found to be stable under stress conditions (higher temperature and higher humidity) for a minimum of 90 days. These results indicate that the product will be stable for about 5 years under normal storage conditions.

We claim:

1. A method for suppressing appetite in a patient in need of such effect comprising administering to said patient an appetite suppressing effective amount of potassium hydroxycitric acid composition comprising less than 2% by weight of potassium hydroxycitric lactone, based on the combined amount of potassium hydroxycitric acid and potassium hydroxycitric lactone.

2. A method for inhibiting cytoplasmic citric lyase in a patient in need of such inhibition comprising administering to said patient a citrate lyase inhibiting effective amount of potassium hydroxycitric acid composition comprising less than 2% by weight of potassium hydroxycitric lactone, based on the combined amount of potassium hydroxycitric acid and potassium hydroxycitric lactone.

3. A method of increasing fat metabolism in a patient in need of such effect comprising administering to said patient a fat metabolism increasing effective amount of potassium hydroxycitric acid composition comprising less than 2% by weight of potassium hydroxycitric lactone, based on the combined amount of potassium hydroxycitric acid and potassium hydroxycitric lactone.

4. A method for causing weight loss in a patient in need of such an effect comprising administering to said patient a weight loss effective amount of potassium hydroxycitric acid composition comprising less than 2% by weight of potassium hydroxycitric lactone, based on the combined amount of potassium hydroxycitric acid and potassium hydroxycitric lactone.

5. A method as recited in claim 4 wherein the potassium hydroxycitric acid is non-hygroscopic.

6. A method for suppressing appetite in a subject in need of such effect comprising administering an appetite suppressing effective amount of potassium hydroxycitric acid composition made by a process comprising:
   a) extracting Garcinia fruit with an alkyl alcohol at least three times to obtain a first extract, a second extract and a third extract;
   b) combining said first extract, said second extract and said third extract to obtain a combined extract;
   c) treating said combined extract with potassium hydroxide and reflux to form potassium hydroxy citrate precipitate;
   d) filtering said precipitate to obtain filtered precipitate;
   e) washing said filtered precipitate with an alkyl alcohol to obtain washed precipitate;
   f) drying said washed precipitate under vacuum to obtain dried precipitate; and
   g) milling, sifting, blending and packing said dried precipitate under nitrogen to obtain said potassium hydroxycitric acid composition.

7. A method for inhibiting cytoplasmic citric lyase in a patient in need of such inhibition comprising administering to said patient a citrate lyase inhibiting effective amount of potassium hydroxycitric acid composition made by a process comprising:
   a) extracting Garcinia fruit with an alkyl alcohol at least three times to obtain a first extract, a second extract and a third extract;
   b) combining said first extract, said second extract and said third extract to obtain a combined extract;
   c) treating said combined extract with potassium hydroxide and reflux to form potassium hydroxycitrate precipitate;
   d) filtering said precipitate to obtain filtered precipitate;
   e) washing said filtered precipitate with an alkyl alcohol to obtain washed precipitate;
   f) drying said washed precipitate under vacuum to obtain dried precipitate; and
   g) milling, sifting, blending and packing said dried precipitate under nitrogen to obtain said potassium hydroxycitric acid composition.

8. A method of increasing fat metabolism in a patient in need of such effect comprising administering to said patient a fat metabolism increasing effective amount of potassium hydroxycitric acid composition made by a process comprising:
   a) extracting Garcinia fruit with an alkyl alcohol at least three times to obtain a first extract, a second extract and a third extract;
   b) combining said first extract, said second extract and said third extract to obtain a combined extract;
   c) treating said combined extract with potassium hydroxide and reflux to form potassium hydroxycitrate precipitate;
   d) filtering said precipitate to obtain filtered precipitate;
   e) washing said filtered precipitate with an alkyl alcohol to obtain washed precipitate;
   f) drying said washed precipitate under vacuum to obtain dried precipitate; and
   g) milling, sifting, blending and packing said dried precipitate under nitrogen to obtain said potassium hydroxycitric acid composition.

9. A method for causing weight loss in a patient in need of such an effect comprising administering to said patient a weight loss effective amount of potassium hydroxycitric acid composition made by a process comprising:
   a) extracting Garcinia fruit with an alkyl alcohol at least three times to obtain a first extract, a second extract and a third extract;
   b) combining said first extract, said second extract and said third extract to obtain a combined extract;
   c) treating said combined extract with potassium hydroxide and reflux to form potassium hydroxycitrate precipitate;
   d) filtering said precipitate to obtain filtered precipitate;
   e) washing said filtered precipitate with an alkyl alcohol to obtain washed precipitate;
   f) drying said washed precipitate under vacuum to obtain dried precipitate, and
   g) milling, sifting, blending and packing said dried precipitate under nitrogen to obtain said potassium hydroxycitric acid composition.

* * * * *